(12) United States Patent
Hafer et al.

(10) Patent No.: US 6,199,553 B1
(45) Date of Patent: Mar. 13, 2001

(54) SURGICAL DRAPE WITH ATTACHABLE FLUID COLLECTION POUCH

(75) Inventors: Greg S. Hafer, Roswell, GA (US); Craig A. Adams; Heather M. Fraley, both of Tuscon, AZ (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/237,765

(22) Filed: Jan. 26, 1999

Related U.S. Application Data

(60) Provisional application No. 60/072,584, filed on Jan. 26, 1998.

(51) Int. Cl.$^7$ .................................................. A61B 19/00
(52) U.S. Cl. .................................................. 128/849; 128/853
(58) Field of Search ...................................... 128/849–856

(56) References Cited

U.S. PATENT DOCUMENTS

| | | |
|---|---|---|
| Re. 34,512 | 1/1994 | Dowdy . |
| 1,491,011 | 4/1924 | Hodgin . |
| 3,072,511 | 1/1963 | Harwood . |
| 3,364,928 | 1/1968 | Creager, Jr. et al. . |
| 3,410,266 | 11/1968 | Krzewinski et al. . |
| 3,484,330 | 12/1969 | Sokolowski et al. . |
| 3,668,050 | 6/1972 | Donnelly . |
| 3,669,106 | 6/1972 | Schrading et al. . |
| 3,721,234 | 3/1973 | Hadtke et al. . |
| 3,791,382 | 2/1974 | Collins . |
| 3,856,006 | 12/1974 | Krzewinski . |
| 3,902,484 | 9/1975 | Winters . |
| 4,027,665 * | 6/1977 | Scrivens ............................. 128/854 |
| 4,033,341 | 7/1977 | Scrivens . |
| 4,041,203 | 8/1977 | Brock et al. . |
| 4,076,017 | 2/1978 | Haswell . |
| 4,089,331 | 5/1978 | Hartigan et al. . |
| 4,119,093 | 10/1978 | Goodman . |
| 4,169,472 | 10/1979 | Morris . |
| 4,323,062 | 4/1982 | Canty . |
| 4,378,794 | 4/1983 | Collins . |
| 4,414,968 | 11/1983 | Amin . |
| 4,489,720 | 12/1984 | Morris et al. . |
| 4,553,538 | 11/1985 | Rafelson . |
| 4,570,628 | 2/1986 | Neal . |
| 4,869,271 | 9/1989 | Idris . |
| 4,891,628 | 1/1990 | Jackson . |
| 5,002,069 * | 3/1991 | Thompson ........................... 128/853 |
| 5,010,899 * | 4/1991 | Thompson ........................... 128/853 |
| 5,074,316 | 12/1991 | Dowdy . |
| 5,151,321 | 9/1992 | Reeves et al. . |
| 5,162,040 | 11/1992 | Annett . |
| 5,222,507 | 6/1993 | Taylor . |
| 5,345,946 | 9/1994 | Butterworth et al. . |
| 5,383,476 | 1/1995 | Peimer et al. . |
| 5,445,165 | 8/1995 | Fenwick . |
| 5,464,024 | 11/1995 | Mills et al. . |
| 5,482,765 | 1/1996 | Bradley et al. . |
| 5,494,050 * | 2/1996 | Reyes ..................................... 128/853 |
| 5,540,979 | 7/1996 | Yahiaoui et al. . |
| 5,599,289 | 2/1997 | Castellana . |
| 5,618,278 | 4/1997 | Rothrum . |
| 5,871,014 * | 2/1999 | Clay ..................................... 128/853 |

FOREIGN PATENT DOCUMENTS 2018597A 10/1979 (GB) .

* cited by examiner

*Primary Examiner*—Michael A. Brown
(74) *Attorney, Agent, or Firm*—Dority & Manning

(57) ABSTRACT

A surgical drape and an attachable fluid collection pouch is provided wherein the surgical drape exhibits a plurality of landing zones suitable for adhesively mounting the fluid collection pouch.

27 Claims, 7 Drawing Sheets

SURGICAL DRAPE WITH ATTACHABLE FLUID COLLECTION POUCH

The present invention is based on provisional patent application Ser. No. 60/072,584 filed Jan. 26, 1998, and priority is hereby claimed therefrom.

FIELD OF THE INVENTION

The present invention relates generally to drapes for covering a patient's body when undergoing an operation or other medical procedure. More specifically, the present invention relates to surgical drapes having an attachable fluid collection pouch for receiving bodily fluids expelled from the body during various surgical procedures.

BACKGROUND OF THE INVENTION

Drapes are used during surgical procedures, in part, to provide a sterile field about the surgical site and during other treatment procedures requiring the maintenance of a sterile environment. When used during surgery, drapes prevent blood and other bodily fluids from cross contaminating the sterile field.

A variety of surgical drapes exist, but most share several common features. Surgical drapes will have one or more openings or apertures (more commonly known in the medical field as "fenestrations") through which the surgical procedure is performed. Most drapes are made of a water-repellent or water-impermeable material, or are coated with such a material, to prevent passage of bodily fluids as well as contaminating microorganisms. Many of today's surgical drapes are made of disposable nonwoven fabrics, plastic film, or papers.

An adhesive material is normally attached to the periphery of the drape material that defines the fenestration(s) so that the drape can be held in place around the surgical site and so that blood will not pass between the drape and the patient's body. The combination of the drape itself and the adhesive material around the perimeter of the aperture ensures a barrier between the surgical wound and the remainder of the body.

During surgical procedures, fairly large amounts of bodily fluids or irrigation liquids are emitted from the fenestrated operating site. If such fluids were allowed to spill over onto the surgical room floor, potentially hazardous slipping situations could occur. In addition, failure to control fluid runoff during surgery could interfere with the sterile field necessary to be maintained during the procedure.

Various means have been developed to absorb, retain and/or collect such fluids. Early surgical procedures often involved the use of absorbent towels to square off the operating site. These towels would in turn act to absorb fluids. Gradually, the designs were improved to include absorbent materials built into the drape itself, including such materials as foam located about the fenestration. When large amounts of fluid were being used or emitted from the incision area, bags and other types of drainage apparatus were employed to channel, collect, or drain the fluids away from the operating site. Examples of such systems can be found in neurological, obstetrical (c-section) and orthopedic (arthroscopy) drapes.

Currently, both disposable non-woven as well as reusable woven surgical drapes are used to create the sterile field for operative procedures. Some drapes employ a primary base sheet in conjunction with a smaller sheet, or pad, that is often made of an absorbent material backed by a liquid impervious film. When used, the reinforcing, absorbent pad is superimposed over the larger base sheet and is often connected thereto with an adhesive. Both the base sheet and the smaller pad have one or more corresponding apertures which define the surgical sites. An example of a surgical drape with a reinforcing, absorbent pad is shown in U.S. Pat. No. 3,902,484 to Winters. If designed correctly, the absorbent area of a surgical drape facilitates cleanup and movement of the patient after the operative procedure.

Various surgical drapes have been developed which employ either an integral or an attachable pouch near the fenestration(s) to collect runoff fluids used or emitted during surgery. For example, U.S. Pat. No. 3,791,382 to Collins shows a drape useful for abdominal surgery where pouches are mounted on either side of the incision area. U.S. Pat. No. 4,089,331 to Hartigan et al. employs a drape with certain fold-back portions that form pockets near the drape fenestration. These pockets are formed on the drape for retaining fluid runoff emanating from the incision site. U.S. Pat. Nos. 3,364,928, 4,076,017, and 4,570,628 to Creager. Jr., et al., Haswell, and Neal, respectively, show the use of various fluid collection devices on drapes employed for performing various vaginal procedures. The collection devices described in these patents are typically plastic bag-like structures that are either formed integrally with, or attached separately to, the top surface of the surgical drape. U.S. Pat. No. 5,464,024 to Mills et al. illustrates another form of a collection pouch that, in some embodiments, is formed on the top surface of the surgical drape so as to completely surround the fenestration and incision site.

Finally, U.S. Pat. No. 5,618,278 to Rothrum, is illustrative of a surgical drape that employs an attachable fluid collection pouch. As shown in the figures of this patent, a collection pouch is provided with an adhesive attachment means for mounting on the top surface of a surgical drape near the fenestration. The plastic pouch has adhesive mounting strips located on its rear surface which, when release material strips covering the adhesive areas are removed, allow the pouch to be adhered to the cloth-like top surface of the surgical drape.

Problems with the adhesive attachments between plastic fluid collection pouches and the top surface of the surgical drapes are sometimes encountered when using such attachable collection pouch devices. As described above, large amounts of fluids may be used near or emitted from the surgical incision site. Often, the fluids will come into contact with the adhesive interface between the fluid collection pouch and the cloth-like absorbent top surface of the surgical drape. (Generally, the collection pouches will actually be mounted on the absorbent reinforcement pads that are mounted on the larger main panel of the surgical drape.) When this occurs, the adhesive bond between the pouch and the cloth-like surface tends to weaken and sometimes may even fail. Obviously, as the collection pouch becomes heavier due to it filling with liquids, more strength is required at the adhesive interface. If the interface completely fails, the potential exists for the pouch to disconnect from the drape and spill over onto the operating floor or otherwise destroy the sterile field.

Thus, there is still a need for further improved surgical drape designs that employ attachable fluid collection pouches. More specifically, there is a need to improve the adhesive interface between such pouches and the drape surface.

SUMMARY OF THE INVENTION

It is an object of the present invention to provide an improved surgical drape for use in surgical procedures.

Another object of the present invention is to provide an improved surgical drape with an attachable fluid collection pouch.

A further object of the present invention is to provide a more substantial adhesive connection interface between the attachable fluid collection pouch and the surface of the surgical drape to which it is attached.

These and other objects are achieved by providing a surgical drape and an attachable fluid collection pouch wherein the surgical drape has a plurality of landing zones suitable for adhesively mounting the fluid collection pouch. Specifically, the drape includes a main panel base sheet defining one or more fenestrations at locations where surgical incisions will occur for the particular operation. An adhesive area surrounds the fenestration and is located on the side of the base sheet which will come into contact with the patient's body. When in place, this pressure-sensitive adhesive maintains the drape in place and forms a closed area between the patient's body and the base sheet to prevent fluids at the operative site from leaking underneath the drape.

A smaller absorbent reinforcement pad with a liquid-impervious backing may be superimposed on the upper surface of the main panel base sheet. The pad has fenestrations through it which match the fenestrations in the base sheet. The pad may be adhered to the base sheet and provides a fluid absorbing sheet for absorbing fluids near the operative site. Both the main panel and the absorbent reinforcement panel have a cut running from their fenestrations to an edge of each sheet.

The aforementioned landing zones for attaching a fluid connection pouch are formed by utilizing the backside, usually liquid-impervious, backing on the smaller absorbent reinforcement pad. These landing zones are formed by utilizing fenestrations in various shapes, such as in a diamond shape. In the particular diamond shape shown in the figures, a fenestration is formed in the smaller absorbent reinforcement pad by cutting the diamond out in segments and not cutting along every edge of the diamond segments, but instead merely perforating certain segment edges. The perforated segment edges are then utilized as fold lines to fold back certain of the diamond segments so that the liquid-impervious backing is exposed on the top surface of the surgical drape. These segments may then be glued, sewn, or otherwise securely attached to the top surface of the absorbent panel and/or main panel base sheet. The collection pouch is then adhesively mounted onto the exposed plastic coated backsides of the fenestration foldback segments to achieve a higher quality adhesive bond than is achieved normally between the pouch and the cloth-like absorbent pad or main panel.

In one embodiment of the present invention, the surgical drape is specifically designed for use during shoulder surgery performed while a patient is in the beach chair, or modified Fowler, position. It will be appreciated, however, that the drape could be formed in various other shapes and utilized for various other procedures.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Figure 1:
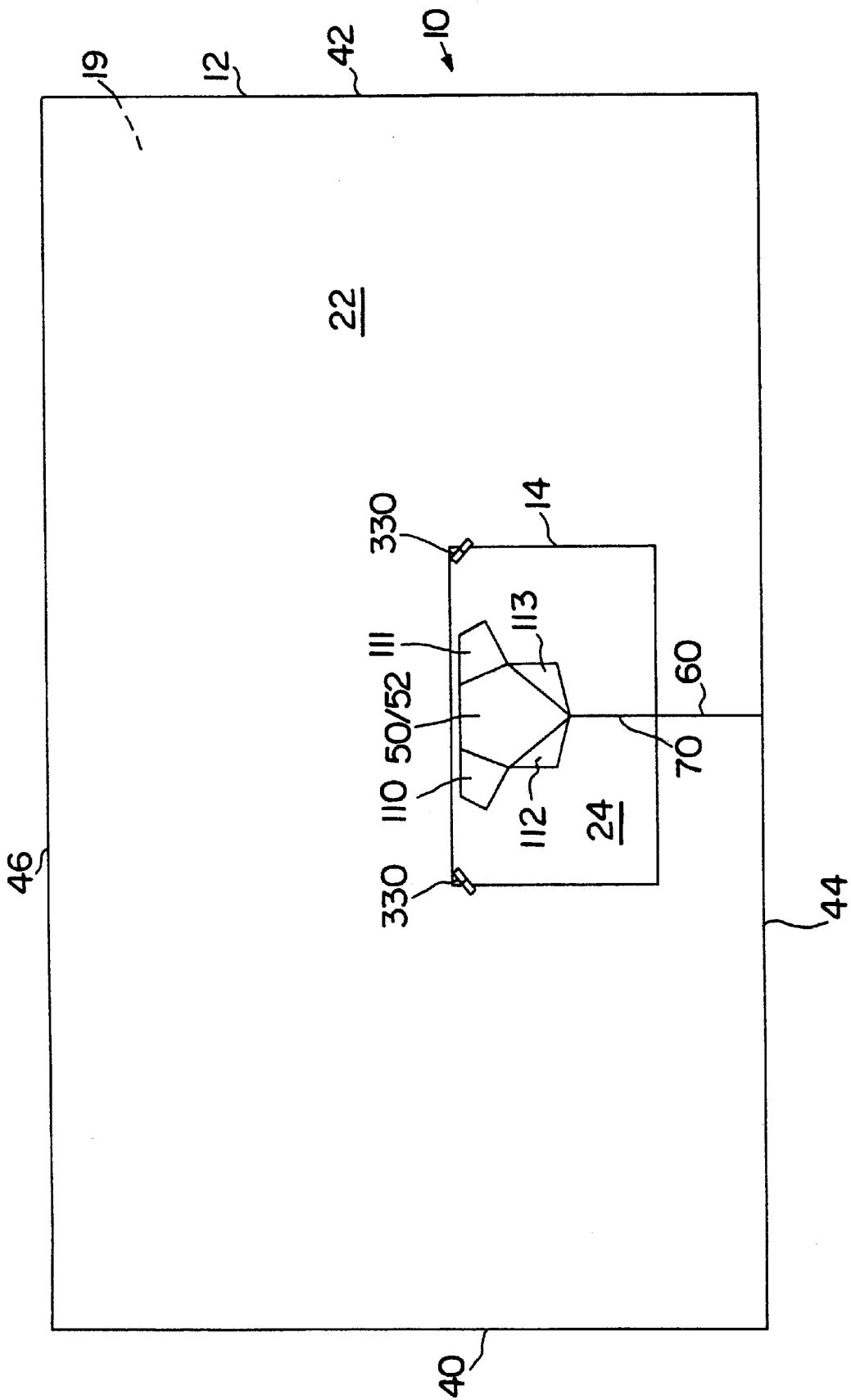
FIG. 1 is a top view of a surgical drape showing the main panel base sheet and smaller reinforcement panel in accordance with an embodiment of the present invention.
Figure 2:
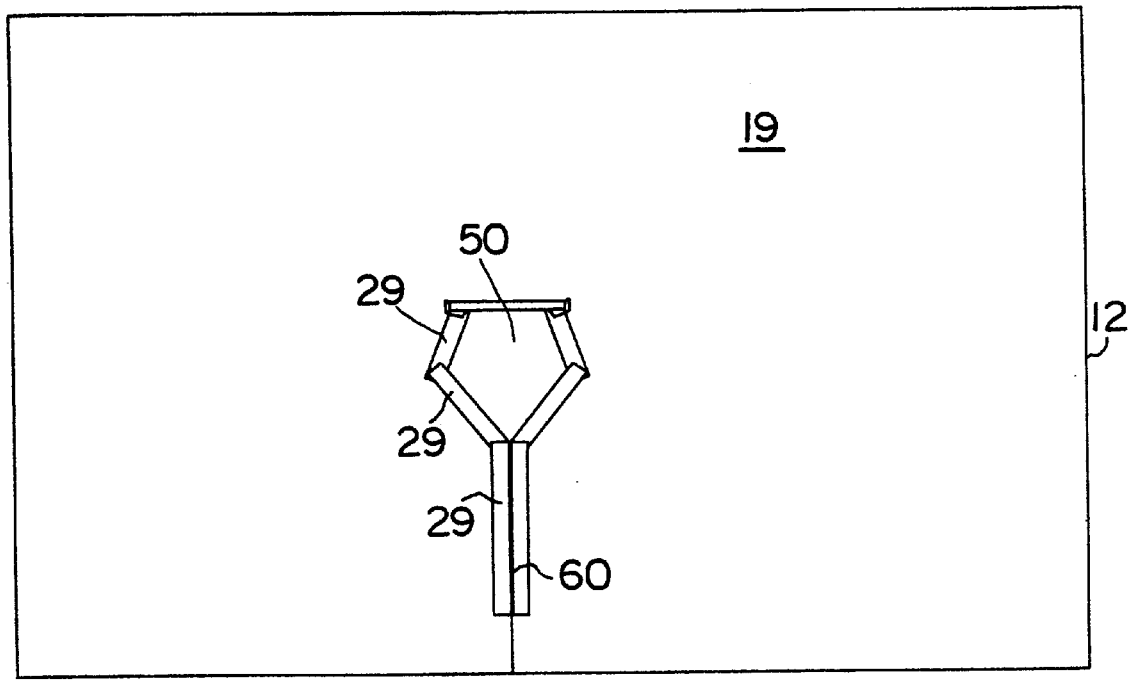
FIG. 2 is view of the backside of the surgical drape of FIG. 1.

Repeat use of reference characters in the present specification and drawings is intended to represent the same or analogous features or elements of the invention.

DETAILED DESCRIPTION OF PREFERRED EMBODIMENT

It is to be understood by one of ordinary skill in the art that the present discussion is a description of exemplary embodiments only, and is not intended as limiting the broader aspects of the present invention, which broader aspects are embodied in the exemplary construction.

Figure 7:
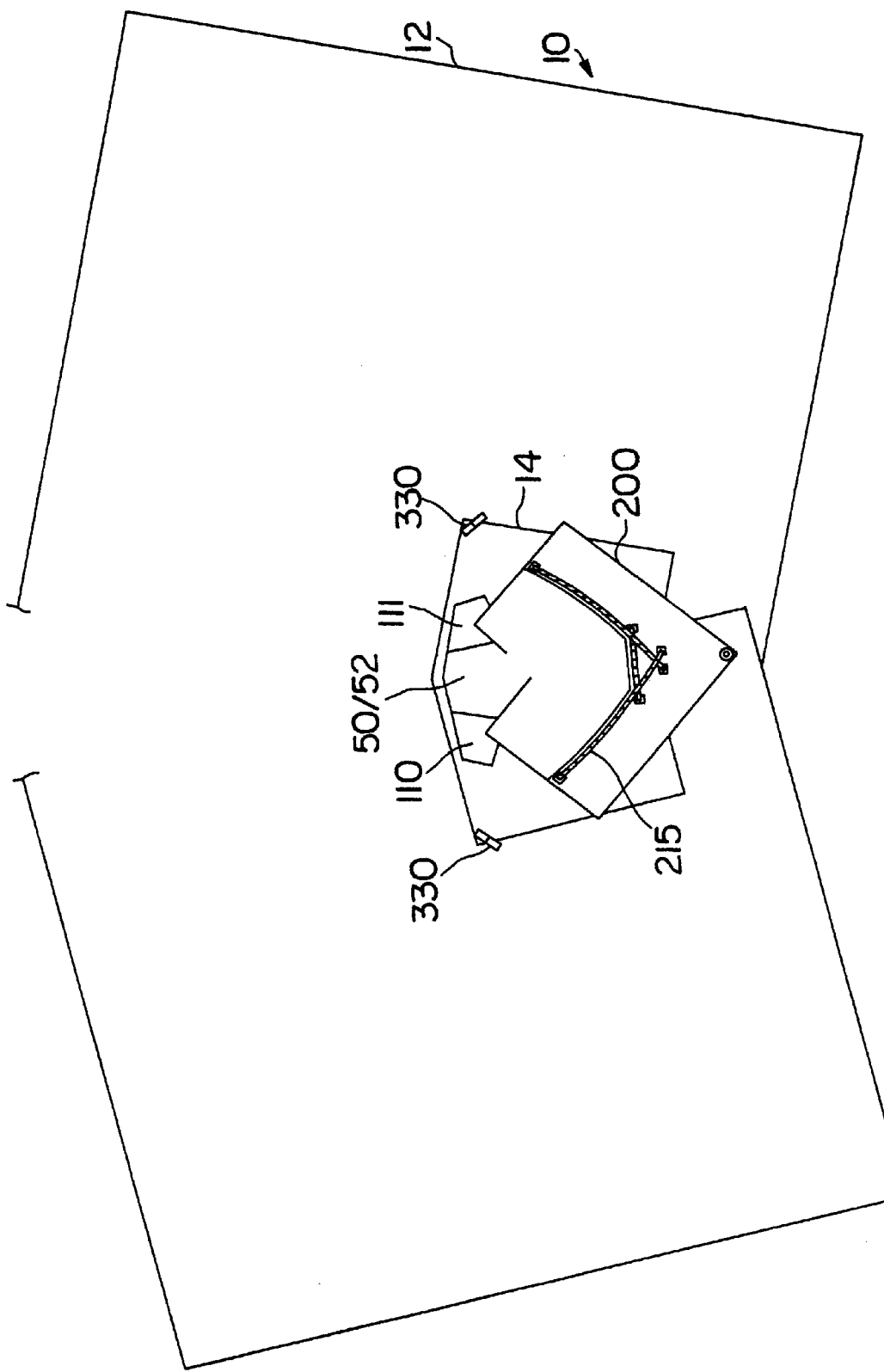
FIG. 7 is a top view of the surgical drape of FIG. 1 illustrating one embodiment having the fluid collection pouch attached to the landing zones on the smaller reinforcement panel.
Figure 8:
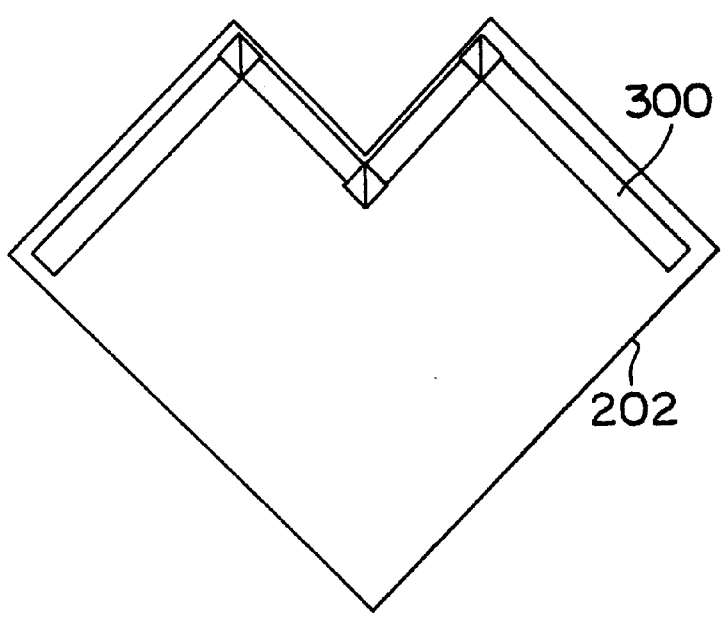
FIG. 8 is a top view of the bottom surface panel of one embodiment of the attachable fluid collection pouch of FIG. 7.

Referring now to FIG. 7, the surgical drape 10 of the present invention is illustrated. Surgical drape 10 includes a main panel base sheet 12, a smaller absorbent reinforcement panel 14, a fluid collection pouch 200, and various optional tubing straps 330. Although it may have varying dimensions and shapes, drape 10 is normally rectangular and sized to cover at least a majority of a patient's body during a surgical procedure. Surgical drape 10 includes one or more apertures, or fenestrations, 50 and 52 that provide the surgeon with access to an operative site on a patient. The various parts of the surgical drape system will now be described in detail.

As shown in FIG. 1, drape 10 is comprised of two sheet materials—a large main panel or base sheet 12 of non-absorbent, nonwoven fabric and a smaller reinforcing pad or panel 14 superimposed on and preferably affixed in some manner to the upper surface 22 of main panel base sheet 12. Reinforcement pad 14 is preferably constructed of a material which has an absorbent upper surface 24 to absorb fluids near the operative site. The reinforcement pad 14 also provides greater resistance to penetration of instruments placed on top of the drape during surgery.

Reinforcement pad 14 is normally made from a fluid-absorbing material backed by a fluid-repellant or fluid-impervious film layer (not shown). The film layer side of the pad 14 is secured to upper surface 22 of main panel base sheet 12 by an adhesive. It is to be understood that various other attachment means, such as sewn seams, could also be employed to effect this attachment. The fluid-absorbing absorbent upper surface 24 of pad 14 remains exposed and available to absorb fluids emitted from the surgical wound.

Preferably, the bottom surface 19 of main panel base sheet 12 has an adhesive material that circumscribes fenestration 50 in main panel base sheet 12 and fenestration 52 in pad 14. The adhesive carried on the bottom surface 19 of main panel base sheet 12 which will be next to the patient's body allows fenestration 50 to be secured around the operative site. The tacky and pressure-sensitive adhesives used may be of any biologically acceptable adhesive. Examples of such adhesive materials are described in U.S. Pat. No. 3,669,106 entitled "Surgical Drape with Adhesive Attachment Means" to Schrading et. al., which is incorporated herein in its entirety by reference. The adhesive carried on the bottom surface 19 of pad 14 adheres drape 10 to the patient's body when the drape is in use to provide a seal around the surgical incision site.

To prevent the adhesive surface of bottom surface 19 from sticking to itself or other portions of drape 10 prior to use, a number of conventional removable release material strips 29, such as wax- or silicone-coated paper, may be placed on the bottom surface 19 of base sheet 12 until the drape is ready for use. In use, the releasable cover sheet is removed and the drape is unfolded over the patient so that the bottom surface 19 of base sheet 12 having the adhesive material is presented toward the patient's body. Once unfolded, the portion of the base sheet 12 extending around the edge of fenestration 50 is pressed onto the patient's skin to create a closed area around the surgical incision site. In addition, the adhesive carried along the back side peripheries of cut 60 through base sheet 12 may be utilized to fold the drape tightly around the patient's body as illustrated in FIG. 7 (without a patient being shown). This is especially important when the drape is used during shoulder surgery and the arm and shoulder of the patient extends through the fenestration 50.

The release material strips 29 may have positioning directions written on their outer surface opposite bottom surface 19. Such directions would normally indicate how the drape is to be placed on the patient. For example, the release material strips may have the word "Head" with an arrow indicating that the drape is to be placed in the arrow direction toward the patient's head.

The large main panel base sheet 12 may be approximately 100"×172" with an upper surface 22 and a bottom surface 19, two opposed ends 40 and 42, and two opposed sides 44 and 46. Fenestrations, or openings, 50 and 52 are cut through the large main panel base sheet 12 and smaller absorbent reinforcement panel 14. In one particular arrangement as shown in FIG. 1, the fenestration 50 is diamond shaped. However, it is contemplated that the fenestration could have various other shapes, particularly when the surgical drape is to be used for purposes other than a beach chair-positioned patient.

Figure 11A:
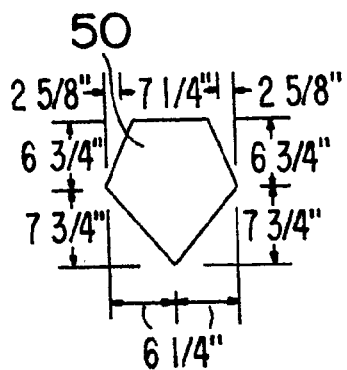
FIGS. 11a and 11b illustrate various suitable measurements for embodiments of the fenestrations useful in the present invention.
Figure 11B:
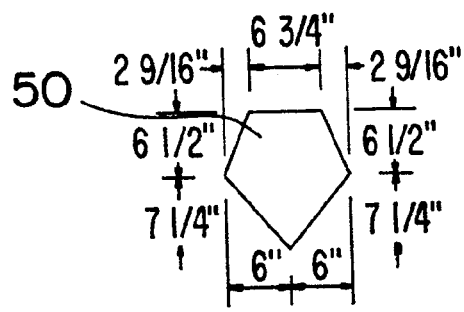

Moreover, fenestration 50 can also be formed to have a variety of dimensions or measurements. For example, FIGS. 11a and 11b illustrate various suitable measurements for embodiments of fenestrations useful in the present invention.

In the diamond-shaped fenestration embodiment, the fenestration 50 may be located at the end-to-end midpoint of main panel 12 and offset approximately 14 inches from the side-to-side midpoint of main panel 12. The long point of the diamond-shaped fenestration 50 points to the nearest side 44 of main panel 12. The main panel 12 is cut from side 44 to the long point of the diamond-shaped fenestration 50 so as to connect the fenestration 50 with the nearest side 44 of main panel 12. The cut 60 is generally perpendicular to the sides 44 and 46 of main panel 12.

Figure 4:
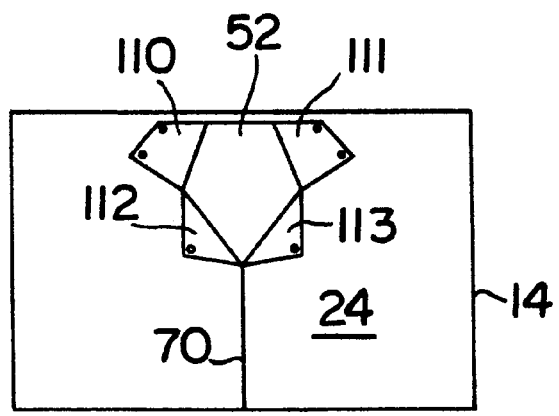
FIG. 4 is a top view of the smaller reinforcement panel of the surgical drape in FIG. 1.

As shown in FIG. 4, the absorbent reinforcement panel 14 may be approximately 30"×48". Fenestration 52 in panel 14 matches fenestration 50 in main panel 12. Reinforcement absorbent panel 14 also includes a cut 70 which generally matches the cut 60 along a partial length.

Figure 6:
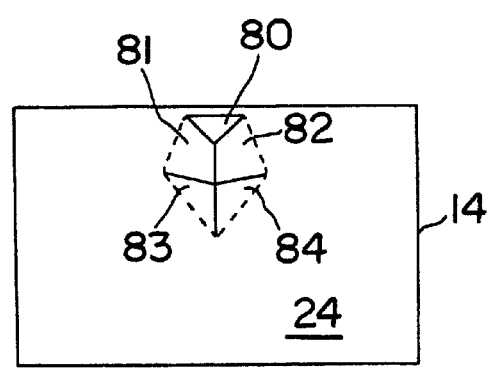
FIG. 6 is a top view of the fenestration portion cutout of FIG. 5 indicating the folding back of various segments in accordance with the present invention.
Figure 3:
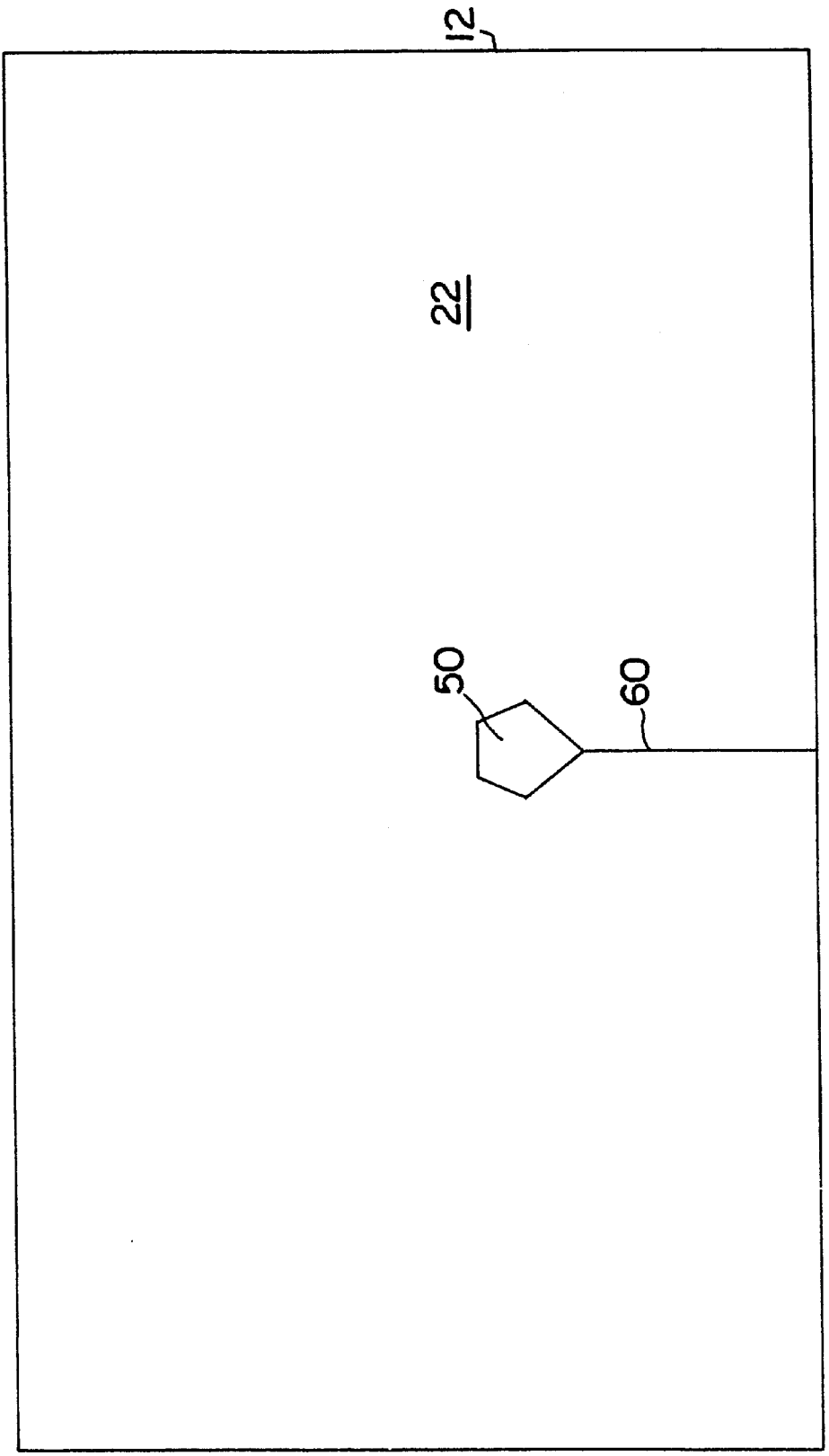
FIG. 3 is a top view of the main panel base sheet of the surgical drape of FIG. 1.
Figure 5:
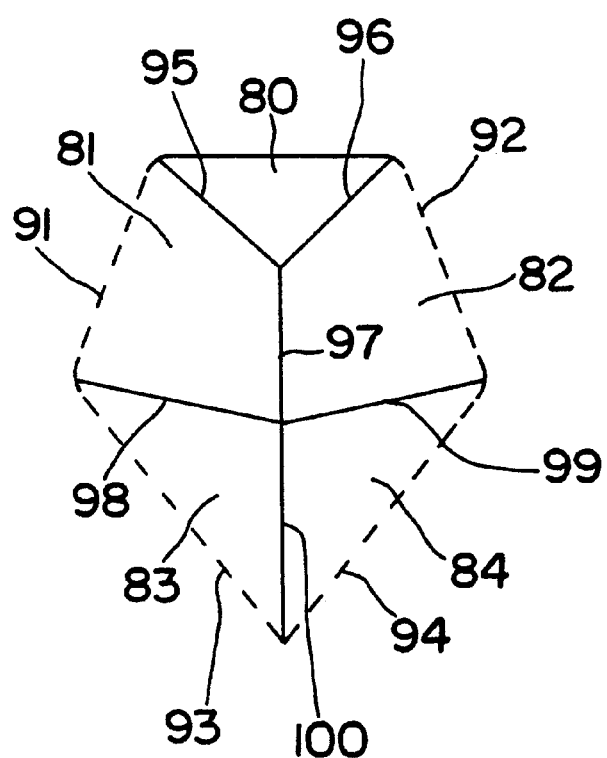
FIG. 5 is a top view of the fenestration portion to be cut into the smaller reinforcement panel of FIG. 4 illustrating the cuts to be made on that panel to obtain the fenestration for one particular embodiment of the present invention.

Fenestration 52 in reinforcement absorbent panel 14 is positioned at the reinforcement absorbent panel's end-to-end midpoint and is offset approximately 7" from the absorbent reinforcement panel's side-to-side midpoint. Unlike the completely cutout fenestration 50 of main panel 12, fenestration 52 of absorbent reinforcement panel 14 is perforated along portions of the fenestration perimeter, and the interior area is cut into segments as shown in FIG. 5. As shown in FIGS. 5 and 6, segment 80 is cut out completely from fenestration 52 and is removed. However, segments 81, 82, 83 and 84 are merely perforated at their edges 91, 92, 93 and 94 which define the periphery of fenestration 52. Segments 81, 82, 83 and 84 are cut apart from each other along cut lines 95, 96, 97, 98, 99 and 100. Segments 81, 82, 83 and 84 are folded back along perforation lines 91, 92, 93 and 94 so as to define the majority of the periphery of fenestration 52. When these panels are folded along the identified perforation lines, they are then glued in place on top surface 24 of reinforcement panel 14. When these segments or panels are folded and glued to top surface 24 in such a manner, the liquid impervious film side backing of absorbent reinforcement panel 14 is exposed around a portion of the periphery of fenestration 52 to form backside surfaces, or "landing zones," 110,111, 112 and 113.

The backside surfaces 110–113 of segments 81, 82, 83 and 84 are used as the attachment surfaces for adhesively attaching the fluid collection pouch. The use of the liquid-impervious backing as landing zones for adhesive attachment of fluid collection pouch 200 (shown in FIGS. 7 and 10) overcomes problems often encountered with presently available fluid collection pouch attachments. In particular, the adhering qualities of the fluid collection pouches previously available would decrease when moisture met the adhesive attachment interface. A liquid impervious/adhesive/plastic attachment formed by the backside of the bottom surface 202 of collection pouch 200 attached through an adhesive layer to the liquid-impervious backing on backside surfaces 110–113 tends to remain in tact even when subjected to fluid attack.

The fluid collection pouch 200 is generally made of a liquid impervious material, such as a clear plastic polyethylene or the like. The fluid collection pouch 200 has an adhesive applied for attachment of the pouch to backside panels 110–113. The adhesive portions prior to attachment to the drape are covered by release material strips 300 to avoid degrading of the adhesive.

Figure 9:
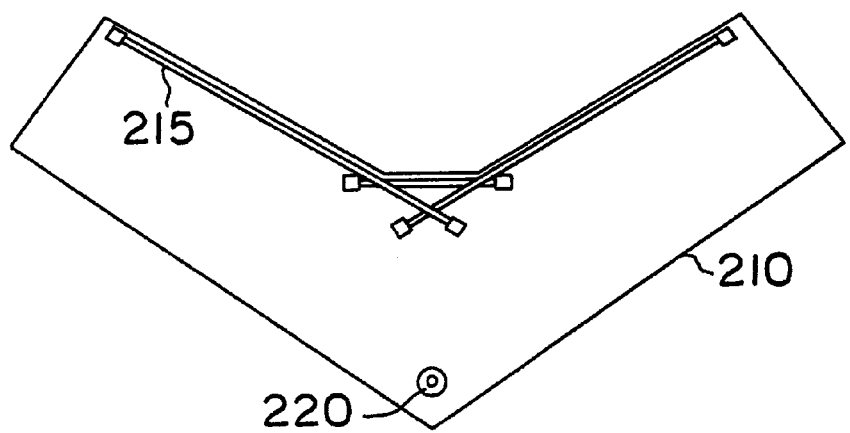
FIG. 9 is a top view of the top surface panel of one embodiment of the attachable fluid collection pouch of FIG. 7.
Figure 10:
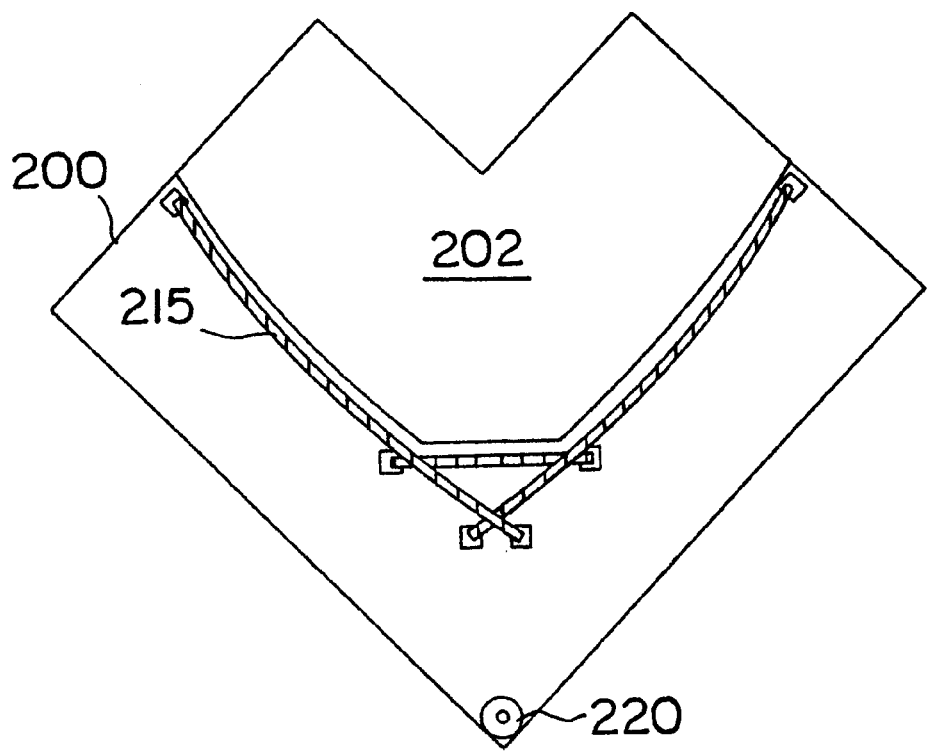
FIG. 10 is a top view of the fluid collection pouch of FIG. 7.

FIG. 9 shows the upper panel 210 that is to be attached to bottom surface 202 to form collection pouch 200. A malleable wire 215 is carried on an upper periphery of upper panel 210 so that collection pouch 200 may be retained in an opened position to allow for collecting of fluid runoff. The entire collection pouch 200 is shown in FIG. 10. A drain 220 may be provide at the lower point of pouch 200 to allow fluid to be drained from pouch 200 during use to prevent overflow.

During use, the drape 10 is placed over a patient, with the arm and shoulder protruding from the fenestration 50. The drape is then folded over itself along cuts 60 and 70 to tightly form the sterile field. The release strips 300 are then removed from the adhesive on bottom surface 202 of fluid collection pouch 200 and fluid collection pouch 200 is then placed in position in contact with the back sides 110–113. This will allow attachment of the fluid collection pouch 200 in a proper position so that fluids expended from the patient during surgery may be collected instead of spilled onto the operating room floor.

Furthermore, as shown in FIGS. 1 and 7, the particular shoulder drape proposed by Kimberly-Clark has two hook-n-loop straps mounted at two adjacent corners of absorbent reinforcement panel 14. These hook-n-loop straps 330 provide adjustable anchorage for surgical lines and suction tubing. The straps 330 allow for adequate securement of such tubing and surgical lines so that they do not interfere with the surgical procedures being performed on the patient.

In one particular embodiment, main panel 12 is comprised of a polypropylene, spunbond-meltblown-spunbond (SMS) nonwoven laminate that is thermally bonded with a wire-weave bond pattern. The laminate normally has a basis weight of 1.95 ounces per square yard (osy) but may range anywhere from about 1.5 osy to about 2.7 osy. Main panel 12 will generally be topically treated for anti-cling, as well as for alcohol repellency.

Absorbent reinforcement panel 14 is typically a spunbond-meltblown-film (SMF) laminate, composed of polypropylene spunbond and meltblown nonwoven layers and a polyethylene-polypropylene copolymer film. Layers may be ultrasonically bonded together. The spunbonded and meltblown components of the laminate may be treated with various treatments such as a Gemtex SM33 to provide a wettable and absorbent structure. The basis weight of the absorbent reinforcement panel 14 may be nominally 3.65 osy, with a range of about 3 osy to about 3.7 osy typically being suitable.

The fluid collection pouch 200 may be formed of any liquid impervious material, such as various clear plastics. The pouch could be opaque but is generally clear so as to provide an indication of the amount and type of fluid being drained into the pouch during surgery. It is generally symmetrical side-to-side. A pouch opening is formed by attaching a smaller front panel 210 to a larger back panel or bottom 202 along four adjacent edges. The top edges are unattached. The unattached top edges of the front panel 210 are reinforced with a malleable wire 215 and form the top front boundaries of the pouch opening. The unattached edges of the larger back piece 202 form the backsplash of pouch 200. Four strips of adhesive, as described previously, are applied to the back side of the pouch along adjacent top edges of back panel 202. The adhesive, as described above, is protected by release paper strips 330 until uncovered for use.

The fluid collection pouch 200 is constructed from a fluid impervious material. Examples of suitable fluid impervious materials include plastic sheet materials of polymers such as acetate, ethylene vinylacetate (EVA), rayon, triacetate, acrylic, aramid, nylon, olefin, e.g., poly(1-butene), polycarbonate, polyethylene, polyester, poly(3-methyl-1-butene), poly(1-pentene), polypropylene, and polystyrene, polysulfone, polytetrafluoroethylene, poly(vinyl alcohol), poly(vinyl chloride), poly(vinylidine chloride), poly (vinylidine fluoride), natural rubber, polyisoprene, polybutadiene, diene styrene copolymers, ethylene propylene copolymers, ethylene propylene diene terpolymers, styrene butadiene block copolymers, styrene isoprene block copolymers, and polyurethane.

Preferred fluid impervious materials may be heat bondable (e.g., so as to allow two sheets to be later sonically joined to provide a fluid impervious joint) and sterilizable (e.g., able to withstand the temperatures, radiation and gases used during the sterilization process which includes temperatures in excess of 60° C. for ethylene oxide sterilization, and temperatures in the range of from 120° to 135° C. for steam sterilization).

Fluid collection pouch 200 may, in one embodiment, be made of a 3 mil thick polyethylene plastic that is assembled using thermal bonding. Reinforcement wire 215 may be malleable, plastic-covered, with a self-adhering back. The attachment adhesive in one particular embodiment may be #1509KC obtained from 3-M Medical Company of St. Paul, Minn.

Other features may be added to the present invention and still fall within its scope. For example, various instrument holding compartments such as that shown in U.S. Pat. No. 5,074,316 to Dowdy as well as non-skid instrument pads such as that described in U.S. Pat. No. 3,856,006 to Krzewinski may be utilized. Other features of the drapes that may be utilized in accordance with the present invention are described in U.S. Pat. No. 4,869,271 to Idris, which is incorporated herein in its entirety by reference.

Drape 10 may be disposable or reusable. Preferably, it is disposable. If disposable, one drape that may be used for this purpose is described in U.S. Pat. No. 3,902,484 entitled "Disposable Surgical Drape" to Winters, which is incorporated herein in its entirety. As described therein, the upper surface 22 of base sheet 12 of the present invention would have the fluid impervious layer or film carried on the backside of pad 14 bonded thereto. This bonding could be by any suitable means such as by an adhesive. Film layer on the back side of reinforcement pad 14 provides a fluid impervious barrier in the primary operative area so that any fluids contacting this area cannot strike through the pad. The absorbency of the remainder of pad 14, including its upper surface 24, allows for some of the fluid run-off to be absorbed while the liquid impervious film layer on the back side of reinforcement pad 14 prevents passage of the fluid to the base sheet 12. In certain embodiments, a pad with a relatively high coefficient of friction on the upper surface may provide a substantially non-slip surface which lessens the chance of accidental falling of surgical instruments and the like placed on the absorbent upper surface 24 of pad 14 during surgery.

The nonwoven fabric from which such base sheets are normally made should be relatively soft and have good draping and folding characteristics. Additionally, the nonwoven fabric should be capable of being subjected to a sterilization treatment without being adversely affected. The use of nonwoven fabrics for disposable drapes eliminates the laundering, resterilization, and handling costs associated with linen drapes.

The selection of a nonwoven fabric having the above-mentioned qualities is within the skill of those working in this art. Materials such as those used in the manufacture of single-use surgical drapes which are usually treated with a water-repellent finish and which may even be treated with a fire-retardant composition, are applicable to the present invention.

Examples of suitable disposable liquid repellent drapable fabrics for making the base sheet include meltblown, spunbond nonwoven fabrics sold by Kimberly-Clark Corporation under the trademark EVOLUTION FABRIC®, described, for example, in U.S. Pat. No. 4,041,203 entitled "Nonwoven Thermoplastic Fabric" to Brock et al. and scrim-reinforced tissue products described for example in U.S. Pat. No. 3,072,511 entitled "Laminated Sheet Material" to Harwood. Other examples of nonwoven fabrics are described in U.S. Pat. No. 3,484,330 entitled "Disposable Fabric" to Sokolowski et. al., U.S. Pat. No. 5,482,765 entitled "Nonwoven Fabric Laminate with Enhanced Barrier Properties" to Bradley et al., and U.S. Pat. No. 5,151,321 entitled "Method of Making Conductive, Water and/or Alcohol Repellent Nonwoven Fabric and Resulting Product" to Reeves et al. The entirety of all five of these patents is incorporated herein by reference.

As for the reinforcing absorbent pad 14, various materials may also be used. The smaller reinforcing pad 14 may be a foam/film laminate of the type described in U.S. Pat. No. 3,669,106 entitled "Surgical Drape with Adhesive Attachment Means" to Schrading and U.S. Pat. No. 3,668,050 entitled "Surgical Drape" to Donnelly. One particularly acceptable pad for this use is described in U.S. Pat. No. 5,540,979 entitled "Porous Non-Woven Bovine Blood-Oxalate Absorbent Structure" to Yahiaoui et al. The entirety of all three of these patents is incorporated herein by reference. Another acceptable pad is made of a spunbond, meltblown material sold under the name CONTROL PLUS® by Kimberly-Clark Corporation.

The film layer on the back side of pad 14 may be anti-static polyethylene, polypropylene, polyethylene methyl acrylate copolymer, or vinyl chloride films. The film provides the described fluid impervious barrier on top of the operative area of base sheet 12 so that any liquid contacting the pad 14 will not strike through to the base sheet 12. In addition, the chosen film will also provide the top surface of the landing zones for attaching the fluid collection pouch of the present invention as described herein. The fluid absorbent material may be bonded to the film layer by any suitable means such as adhesive bonding, fusing or by extruding the film directly. Examples of suitable absorbent materials include polyester and polyether polyurethane foams, with thicknesses anywhere in the range of from about 25 mils to about 100 mils.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A surgical drape for covering a patient during a surgical procedure, said drape comprising:
    a) a base sheet having an upper surface and a lower surface, said base sheet defining a fenestration therein through which said surgical procedure will be preformed when said drape is covering a patient during a surgical procedure;
    b) an absorbent reinforcement pad having an absorbent upper surface and a liquid-repellant lower surface, said absorbent reinforcement pad being superimposed on said base sheet and having its liquid-repellant lower surface mounted on the upper surface of said base sheet, said absorbent reinforcement pad defining a fenestration therein which, when said pad is mounted on said base sheet, forms an aperture through said base sheet and said reinforcement pad through which surgical procedures may be performed; and
    c) wherein said reinforcement pad has a landing zone for allowing a fluid collection device to be positioned on said absorbent upper surface of said reinforcement pad to collect and retain fluids exuded near said aperture during surgical procedures, said landing zone being formed from a material that will allow for adhesive attachment of said fluid collection device to said landing zone at an adhesive interface that will not fail during surgical procedures when fluids are exuded near said aperture and collected in said fluid collection device, said landing zone comprising a portion of the liquid-repellant lower surface of said reinforcement pad, said pad portion having been exposed by being folded back to form said reinforcement pad fenestration.

2. The surgical drape as defined in claim 1 wherein said base sheet defines a cut therein that extends from said fenestration to an edge of said base sheet and wherein said reinforcement pad defines a cut therein that extends from said fenestration to an edge of said reinforcement pad, said reinforcement pad being further superimposed on said base sheet so that said cut on said base sheet and said cut on said reinforcement pad match along a portion of their lengths.

3. The surgical drape as defined in claim 2 wherein said base sheet comprises an adhesive area surrounding said base sheet cut on said lower surface of said base sheet so that said base sheet may be further adhesively joined to said patient during a surgical procedure.

4. The surgical drape as defined in claim 1 wherein said base sheet further comprises an adhesive area surrounding said base sheet fenestration on said lower surface of said base sheet so that said base sheet may be adhesively joined to said patient during a surgical procedure.

5. The surgical drape as defined in claim 3 wherein said base sheet comprises a further adhesive area surrounding said base sheet cut on said lower surface of said base sheet.

6. The surgical drape as defined in claim 1 wherein said landing zone comprises a portion of the liquid-repellant lower surface of said reinforcement pad which portion has been exposed by being folded back during formation of said reinforcement pad fenestration.

7. The surgical drape as defined in claim 1 wherein said liquid-repellant lower surface of said reinforcement pad is adhesively mounted on the upper surface of said base sheet.

8. The surgical drape as defined in claim 1 wherein said liquid-repellant lower surface of said reinforcement pad is sewn to said upper surface of said base sheet.

9. The surgical drape as defined in claim 1 further comprising a fluid collection device mounted to said absorbent reinforcement pad by being adhesively attached to said landing zone.

10. The surgical drape as defined in claim 1 wherein said fluid collection device is made from a liquid-impervious material.

11. The surgical drape as defined in claim 10 wherein said fluid collection device is a pouch having a liquid impervious back panel and a liquid impervious front panel, said liquid impervious front panel having malleable strips of wire carried on the upper periphery thereof to allow the front panel to be maintained in an open position.

12. The surgical drape as defined in claim 10 wherein said fluid collection device is a pouch having a liquid impervious back panel and a liquid impervious front panel, said liquid impervious front panel having a drain thereon to allow fluid to be drained from said pouch during a surgical procedure to prevent overflow.

13. The surgical drape as defined in claim 1 further comprising anchors for maintaining surgical lines and suction tubing in position during surgical procedures.

14. The surgical drape as defined in claim 13 wherein said anchors comprise hook-n-loop straps that are mounted at two adjacent corners of said absorbent reinforcement pad.

15. The surgical drape as defined in claim 1 wherein said base sheet comprises a polypropylene, spunbond-meltblown-spunbond nonwoven laminate.

16. The surgical drape as defined in claim 15 wherein said laminate has a basis weight of between about 1.5 osy to about 2.7 osy.

17. The surgical drape as defined in claim 1 wherein said absorbent reinforcement pad comprises a spunbond-meltblown-film laminate.

18. The surgical drape as defined in claim 17 wherein said absorbent reinforcement pad has a basis weight of between about 3 osy to about 3.7 osy.

19. The surgical drape as defined in claim 1 wherein said surgical drape is shaped to allow surgical procedures to be performed on a patient's shoulder.

20. A surgical drape for covering a patient during a surgical procedure, said drape comprising:
   a) a base sheet having an upper surface and a lower surface, said base sheet defining a base sheet fenestration therein through which said surgical procedure will be performed when said drape is covering said patient during a surgical procedure, said base sheet having a base sheet cut therein that extends from said fenestration to an edge of said base sheet, said base sheet having adhesive areas surrounding said base sheet fenestration and said base sheet cut for adhesively attaching said base sheet to a patient during a surgical procedure;
   b) an absorbent reinforcement pad having an absorbent upper surface and a liquid-repellant lower surface, said absorbent reinforcement pad being superimposed on said base sheet and having its liquid-repellant lower surface mounted on the upper surface of said base sheet, said absorbent reinforcement pad defining a fenestration therein which, when said pad is mounted on said base sheet, creates an aperture through said base sheet and said reinforcement pad through which surgical procedures may be performed, said reinforcement pad having a cut therein that extends from said fenestration to an edge of said reinforcement pad, said reinforcement pad being further superimposed on said base sheet so that said cut on said base sheet and said cut on said reinforcement pad match along a portion of their lengths;
   c) wherein said reinforcement pad has a landing zone for allowing a fluid collection device to be positioned on said absorbent upper surface of said reinforcement pad to collect and retain fluids exuded near said aperture during surgical procedures, said landing zone being formed from a material that will allow for adhesive attachment of said fluid collection device to said landing zone at an adhesive interface that will not fail during surgical procedures when fluids are exuded near said aperture and collected in said fluid collection device, said landing zone comprising a portion of said liquid-repellant lower surface of said reinforcement pad which has been exposed by being folded back to form said reinforcement pad fenestration; and
   d) a fluid collection device positioned on and adhesively attached to said absorbent reinforcement pad at said landing zone to provide a pouch for collecting fluids exuded from near said aperture.

21. The surgical drape as defined in claim 20 wherein said fluid collection device is a pouch having a liquid impervious back panel and a liquid impervious front panel, said liquid impervious front panel having malleable strips of wire carried on the upper periphery thereof to allow the front panel to be maintained in an open position.

22. The surgical drape as defined in claim 20 wherein said fluid collection device is a pouch having a liquid impervious back panel and a liquid impervious front panel, said liquid impervious front panel having a drain thereon to allow fluid to be drained from said pouch during a surgical procedure to prevent overflow.

23. The surgical drape as defined in claim 20 further comprising anchors for maintaining surgical lines and suction tubing in position during surgical procedures.

24. The surgical drape as defined in claim 23 wherein said anchors comprise hook-n-loop straps that are mounted at two adjacent corners of said absorbent reinforcement pad.

25. The surgical drape as defined in claim 20 wherein said base sheet comprises a polypropylene, spunbond-meltblown-spunbond nonwoven laminate.

26. The surgical drape as defined in claim 20 wherein said absorbent reinforcement pad comprises a spunbond-meltblown-film laminate.

27. The surgical drape as defined in claim 20 wherein said surgical drape is shaped to allow surgical procedures to be performed on a patient's shoulder.

\* \* \* \* \*